(12) United States Patent
Orinski (10) Patent No.: US 8,538,530 B1
(45) Date of Patent: Sep. 17, 2013

(54) HERMETICALLY SEALED FEEDTHROUGH CASE

(75) Inventor: William G. Orinski, Reno, NV (US)

(73) Assignee: Advanced Bionics, Valencia, CA (US)

(*) Notice: Subject to any disclaimer, the term of this patent is extended or adjusted under 35 U.S.C. 154(b) by 491 days.

(21) Appl. No.: 12/610,567

(22) Filed: Nov. 2, 2009

Related U.S. Application Data (60) Provisional application No. 61/116,261, filed on Nov. 19, 2008.

(51) Int. Cl.
*A61N 1/00* (2006.01)

(52) U.S. Cl.
USPC .......................................................... 607/36

(58) Field of Classification Search
USPC .......................................................... 607/36
See application file for complete search history.

(56) References Cited

U.S. PATENT DOCUMENTS

| | | | |
|---|---|---|---|
| 4,213,004 A | | 7/1980 | Acker et al. |
| 5,333,095 A | | 7/1994 | Stevenson et al. |
| 5,750,926 A | | 5/1998 | Schulman et al. |
| 5,782,891 A | | 7/1998 | Hassler et al. |
| 6,008,980 A | * | 12/1999 | Stevenson et al. ............ 361/302 |
| 7,142,909 B2 | | 11/2006 | Greenberg et al. |
| 7,190,051 B2 | | 3/2007 | Mech et al. |
| 7,211,103 B2 | | 5/2007 | Greenberg et al. |
| 7,257,446 B2 | | 8/2007 | Greenberg et al. |
| 7,291,540 B2 | | 11/2007 | Mech et al. |
| 2003/0109903 A1 | * | 6/2003 | Berrang et al. ................. 607/36 |
| 2009/0034769 A1 | | 2/2009 | Darley et al. |
| 2010/0292760 A1 | | 11/2010 | Leigh et al. |

FOREIGN PATENT DOCUMENTS

| | | |
|---|---|---|
| WO | 2006081361 A2 | 8/2006 |
| WO | 2006081361 A3 | 4/2007 |
| WO | 2007070989 A1 | 6/2007 |

OTHER PUBLICATIONS

Adtech Ceramics, Design & Capabilities Guide, Ceramic Packages-Chemical Milling- Injection Molding, Advanced Technical Ceramics Company 2007.

* cited by examiner

*Primary Examiner* — Christopher D Koharski
*Assistant Examiner* — Nadia Ahmad
(74) *Attorney, Agent, or Firm* — Steven L. Nichols; Van Cott, Bagley, Cornwall & McCarthy P.C.

(57) ABSTRACT

An implantable medical device includes a housing component comprising a flexure; and a ceramic feedthrough attached to the flexure such that the flexure reduces transmission of forces from housing component to the ceramic feedthrough. According to one illustrative embodiment, the implantable medical device is a cochlear implant which includes a titanium feedthrough case made up of a body portion and a flexure; and a ceramic feedthrough being hermetically joined to the flexure by an active braze, the flexure reducing transmission of forces from the titanium feedthrough case to the ceramic feedthrough.

19 Claims, 8 Drawing Sheets

*Fig. 10* ously filed U.S. provisional patent application No. 61/116,261, filed Nov. 19, 2008 and entitled "Hermetically Sealed FeedThrough Case," which application is hereby incorporated by reference in its entirety.

HERMETICALLY SEALED FEEDTHROUGH CASE

RELATED APPLICATIONS

The present application claims priority under 35 U.S.C. §119(e) of a previously filed U.S. provisional patent application No. 61/116,261, filed Nov. 19, 2008 and entitled "Hermetically Sealed FeedThrough Case," which application is hereby incorporated by reference in its entirety.

BACKGROUND

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also amenable to alleviation by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with complete sensorineural hearing loss are unable to derive any benefit from conventional hearing aid systems no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems or cochlear prostheses have been developed that can bypass the hair cells located in the vicinity of the radially outer wall of the cochlea by presenting electrical stimulation directly to the auditory nerve fibers. This leads to the perception of sound in the brain and provides at least partial restoration of hearing function. Thus, most of these cochlear prosthesis systems treat sensorineural deficit by stimulating the ganglion cells in the cochlea directly using an implanted electrode or lead that has an electrode array. Thus, a cochlear prosthesis operates by directly stimulating the auditory nerve cells, bypassing the defective cochlear hair cells that normally transduce acoustic energy into electrical activity to the connected auditory nerve cells.

Prior to stimulating the nerve cells, the electronic circuitry and the electrode array of the cochlear prosthesis separate acoustic signal into a number of parallel channels of information, each representing a narrow band of frequencies within the perceived audio spectrum. Ideally, each channel of information should be conveyed selectively to a subset of auditory nerve cells that normally transmit information about that frequency band to the brain. Those nerve cells are arranged in an orderly tonotopic sequence, from the highest frequencies at the basal end of the cochlear spiral to progressively lower frequencies towards the apex.

Consequently, a cochlear prosthesis may typically comprise both an external unit that receives and processes ambient sound waves and an implant that receives data from the external unit and uses that data to directly stimulate the auditory nerve.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

Implantable medical devices (IMD's) detect and/or deliver therapy for a variety of medical conditions. By way of example and not limitation, implantable medical devices can include pulse generators, cardioverter-defibrillators, infusion pumps, vagus nerve stimulators, cochlear implants, spinal cord stimulators, and other implants. In the present specification, a cochlear implant is used as an example of an implantable medical device.

These implants have stringent toxicity and reliability requirements. In most cases, malfunction or mechanical failure requires surgical extraction. Reducing the size and weight of the implanted devices is also a major consideration.

Electronic circuitry and components are present in most implanted medical devices. To protect the electronics from corrosion and shorting, the electronics are typically encapsulated in a hermetically sealed housing. In some embodiments, there are multiple mechanisms or layers used in the container design to isolate the electronics or other components from contact with the body tissues and fluids.

The failure of the hermetically sealed housing can allow the ingress of body fluids into the electronics. The presence of body fluid within the housing can lead to failure of the implanted medical device. The failure of some medical devices, such as pacemakers and defibrillators, can be life threatening. In other circumstances, the failure of an implanted medical device may interrupt therapy needed for the day-to-day functioning of a patient.

The failure of a hermetically sealed housing in an implant can result from a variety of conditions and events. The ingress of body fluid and/or humidity can occur along joints and electrical wires that pass through the sealed housing. For some implants, particularly those located subcutaneously, and especially adjacent bone, the ability of the hermetically sealed housing to withstand impact is particularly important.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example" or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Throughout the specification, a cochlear implant is used as just one example of an implanted medical device. The principles discussed in the present specification can be applied to a wide range of implanted medical devices.

Figure 1:
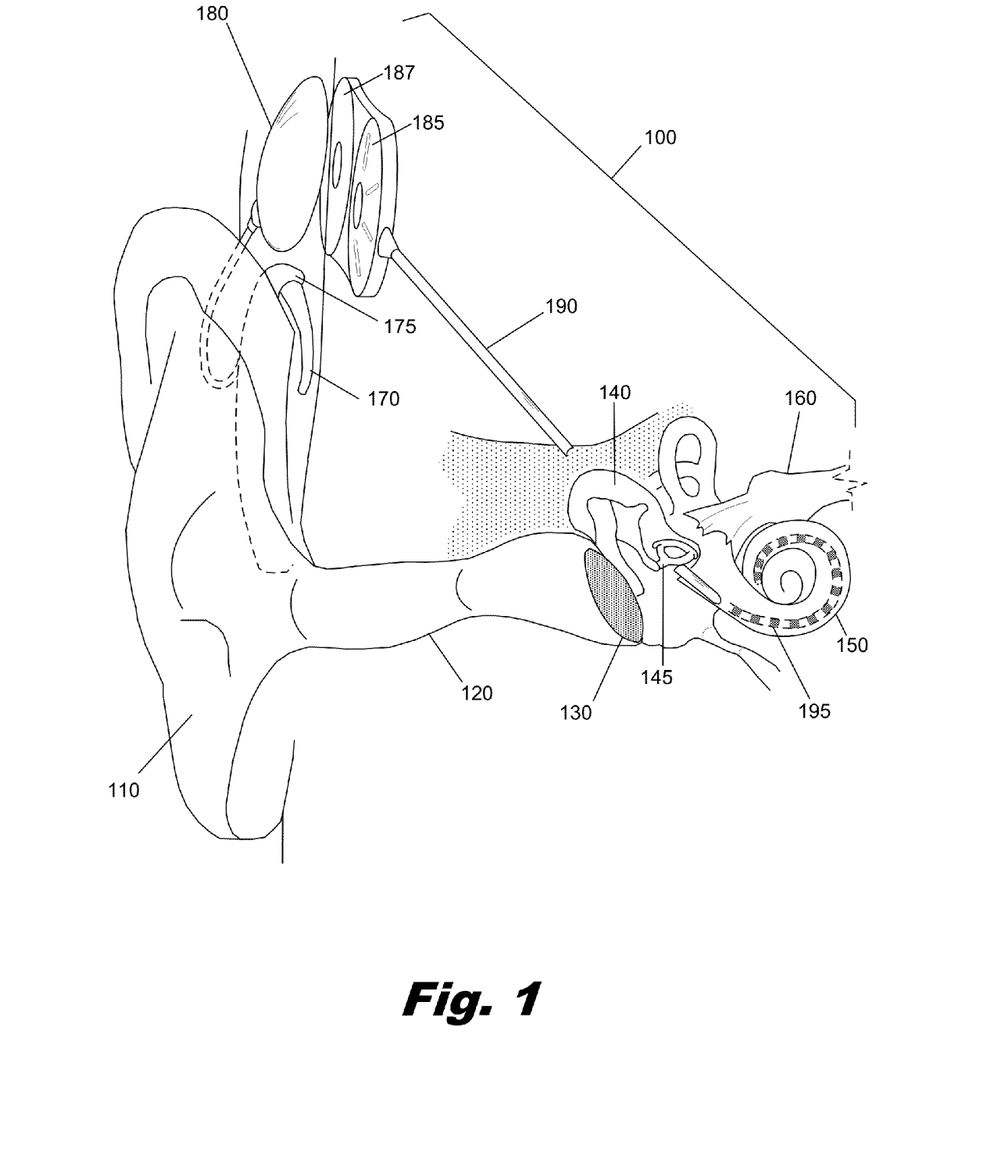
FIG. 1 is an illustrative diagram showing an illustrative cochlear implant system, according to one embodiment of principles described herein.

FIG. 1 is a diagram showing one illustrative embodiment of a cochlear implant (100) surgically placed within the patient's auditory system. Ordinarily, sound enters the outer ear (110) and is directed into the auditory canal (120) where the sound wave vibrates the tympanic membrane (130). The motion of the tympanic membrane is amplified and transmitted through the ossicular chain (140) which consists of three bones in the middle ear. The third of the ossicles, or stirrup, (145) contacts the outer surface of the cochlea (150) and causes movement of the fluid within the cochlea (150). Cochlear hair cells respond to the fluid-borne vibration in the cochlea (150) and trigger neural electrical signals that are conducted from the cochlea (150) to the auditory cortex by the auditory nerve (160).

As indicated above, the cochlear implant (100) is a surgically implanted electronic device that provides a sense of sound to a person who is profoundly deaf or severely hard of hearing. As also noted above, in many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from sensorineural hearing loss.

Unlike hearing aids, the cochlear implant (100) does not amplify sound, but works by directly stimulating any functioning auditory nerve cells inside the cochlea (150) with electrical impulses. Consequently, providing a cochlear prosthesis typically involves the implantation of electrodes into the cochlea. The cochlear prosthesis operates by direct electrical stimulation of the auditory nerve cells, bypassing the defective cochlear hair cells that normally traduce acoustic energy into electrical energy.

External components of the cochlear implant include a microphone (170), speech processor (175), and transmitter (180). The microphone (170) picks up sound from the environment and converts it into electrical impulses. The speech processor (175) selectively filters and manipulates the electrical impulses and sends the processed electrical signals through a cable to the transmitter (180). The transmitter (180) receives the processed electrical signals from the processor (175) and transmits them to the receiver (185) by electromagnetic induction and/or by using radio frequencies.

The internal components of the cochlear implant may include an antenna (187) and an internal processor (185). The antenna (187) and internal processor (185) are secured beneath the user's skin, typically above and behind the external ear (110). The internal processor (185) includes electronic circuitry housed in a hermetically sealed enclosure. This electronic circuitry is connected to via a hermetically sealed feedthrough to the antenna (187). The antenna (187) receives power and signals from the transmitter (180) via electromagnetic induction and/or radio frequency signals. In some cochlear implants, the transmitter (180) is held in place by magnetic interaction with the underlying antenna (187). The internal processor (185) processes the received signals and sends modified signals through the hermetic feedthrough to cochlear lead (190) and electrodes (195). The electrodes (195) are wound through the cochlea (150) and provide direct electrical stimulation to the auditory nerve inside the cochlea (150).

The implant works by using the tonotopic organization of the basilar membrane of the inner ear. The tonotopic organization, also referred to as "frequency- to-place" mapping, is the way the ear differentiates between sounds of different frequencies. In a normal ear, sound vibrations in the air are converted into resonant vibrations of the liquid within the cochlea. High-frequency sounds do not pass very far through the liquid and the structures of the cochlea that contain the liquid. Low-frequency sounds pass farther down the cochlear channels. Consequently, the nerve cells at the basal end of the cochlear spiral sense higher frequencies, while progressively lower frequencies are sensed at different portions of the cochlear spiral moving towards the apex. The movement of hair cells located all along the basilar membrane stimulates the surrounding nerve cells which conduct electrical impulses to the brain. The brain is able to interpret the nerve activity to determine which area of the basilar membrane is resonating and, therefore, what sound frequencies are being heard.

For individuals with sensorineural hearing loss, hair cells are often fewer in number and/or damaged. The cochlear implant bypasses the hair cells and stimulates the cochlear nerves directly using electrical impulses. The cochlear implant stimulates different portions of the cochlea (150) according to the sound detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figure 2:
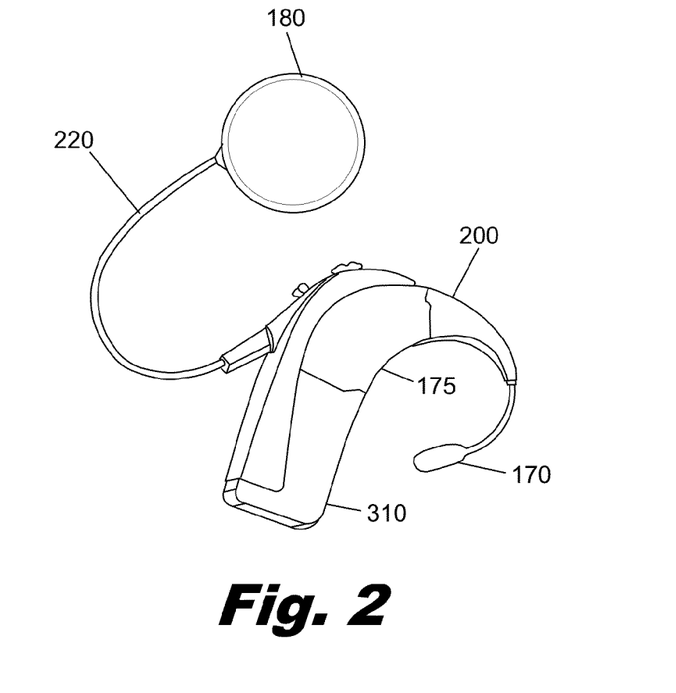
FIG. 2 is an illustrative diagram showing the external components of an illustrative cochlear implant system, according to one embodiment of principles described herein.

FIG. 2 shows one illustrative embodiment of the external components of the cochlear implant. The microphone (170) is attached to the ear hook (200). The ear hook (200) secures the external components behind the outer ear. The microphone (170) senses environmental sounds and converts those sounds into electrical impulses. The processor (175) filters and manipulates the electrical impulses it receives from the microphone (170) and transmits processed electrical sound signals along the external cable (320) to the transmitter (180). The processor (175), microphone (170) and transmitter (180) are powered by a battery (310).

Figure 3:
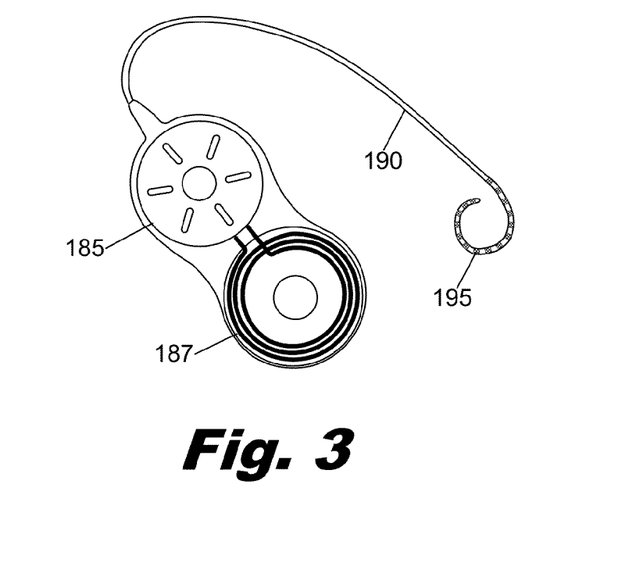
FIG. 3 is an illustrative diagram showing the implanted components of an illustrative cochlear implant system, according to one embodiment of principles described herein.

FIG. 3 shows one illustrative embodiment of the internal components of the cochlear implant device. As described above, the antenna (187) is connected to the internal processor (185). According to one embodiment, the antenna (187) is a coiled wire or wires that are encapsulated by a silicone overcoat. A cavity within the center portion of the antenna (187) is adapted to receive a magnet, which provides the magnetic force required to hold the external transmitter (180) in place over the antenna (187). The internal processor (185) is electrically connected to antenna (187) and receives signals and power via the antenna (187). The internal processor (185) is connected to the cochlear lead (190) which terminates in a flexible end that contains the electrodes (195). The electrodes (195) consist of a plurality of individual electrodes contacts made from platinum or at a similarly high conductive material. These electrodes and associated wires are supported and connected by a flexible and durable biocompatible material, typically silicone rubber.

Figure 4:
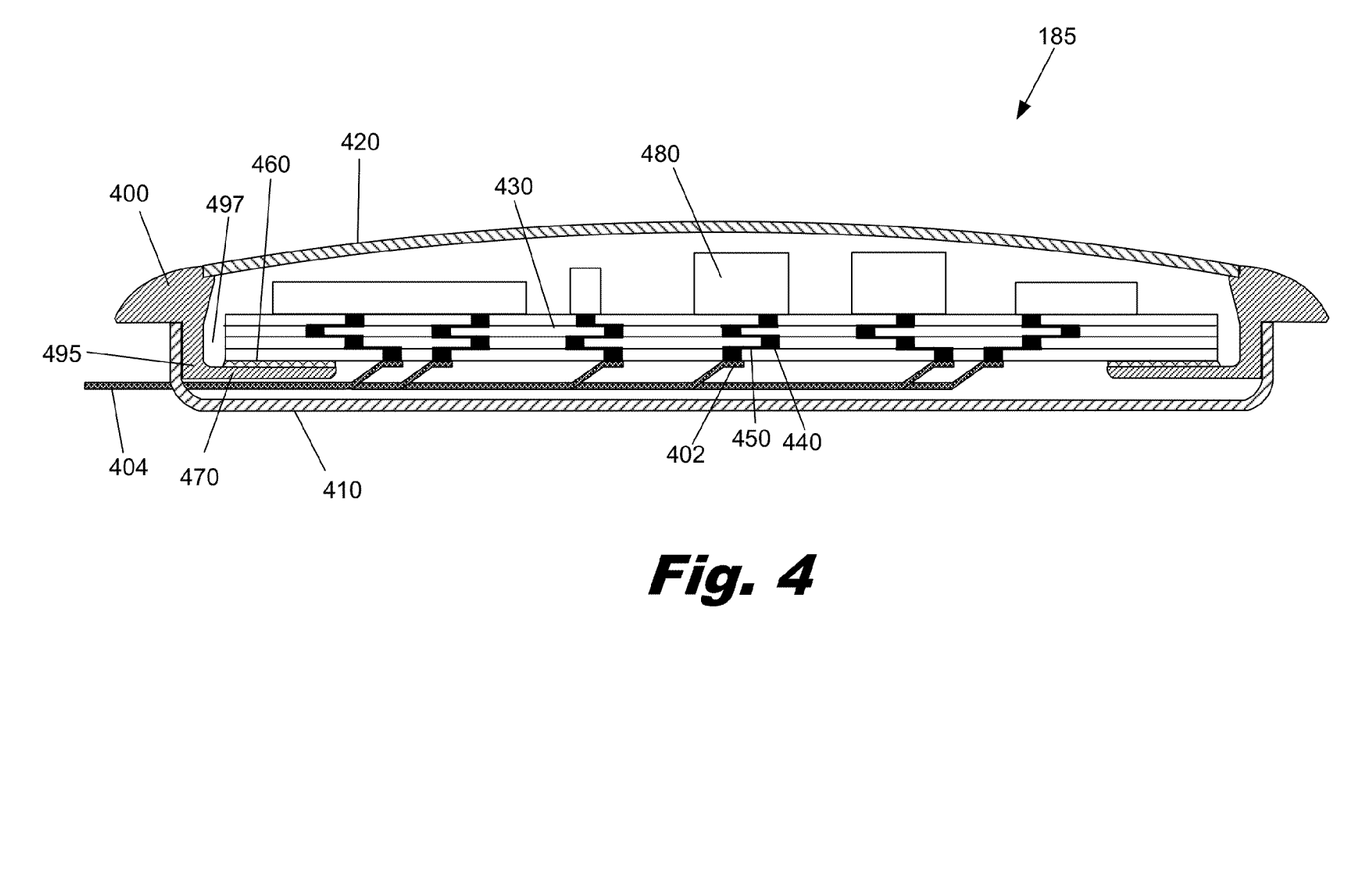
FIG. 4 is a cross-sectional view of an illustrative internal processor of a cochlear implant, according to one embodiment of principles described herein.

FIG. 4 is a cross-sectional view of an illustrative internal processor (185). The internal processor (185) includes a number of components, such as electronics (480), which may be sensitive to moisture or other substances contained within the surrounding tissue. According to one embodiment, these electronics (480) and other sensitive components are sealed within a hermetic enclosure which is made up of a feedthrough case (400), a top cover (420), and a multilayer ceramic feedthrough (430). These three components (400, 420, 430) are connected to form the hermetically sealed enclosure. The feedthrough case (400) serves as a primary structural component and connects the top cover (420) and multilayer ceramic feedthrough (430). The feedthrough case (400) may include a first portion (495) that is downwardly extending and a second portion (470) that extends inwardly toward the center of the case (400). A bottom cover (410) is joined to the feedthrough case (400) and covers the bottom of the ceramic feedthrough (430) but does not necessarily provide a hermetic seal since the cable or coil (404) exits the bottom cover to couple to the electrodes (195, FIG. 3).

In one illustrative embodiment, the feedthrough case (400) is machined out of a single piece of medical grade titanium. The top cover (420) and the bottom cover (410) can be stamped out of titanium sheet stock. The feedthrough case (400) may be joined to the top cover (420) using a variety of methods that create a hermetically sealed joint. By way of example and not limitation, the feedthrough case (400) may be attached to the top cover using laser welding. As discussed above, the feedthrough case (400), top cover (420), and ceramic feedthrough (430) form the hermetically sealed enclosure which serves as the primary method of restricting body fluids from reaching the electronics housed within the internal processor (185). The bottom cover (410) is joined to the feedthrough case, such as by welding. According to one illustrative embodiment, an additional layer of protection can be provided by encapsulating the entire internal processor (185) and antenna (187) in a silicone overcoat. The silicone overcoat provides additional protection against fluid ingress, helps prevent excessive flexure of wired connections, and forms a mechanically compliant biocompatible coating that protects the implanted components and makes the implant more comfortable for the users.

However, the silicone overcoat typically does not form a long term hermetic protection against ingress of fluids. There can still be a significant chance of fluid ingress through or along the electrical wires and connections which pass through the silicone overcoat. To prevent fluid ingress while still maintaining electrical conductivity, a ceramic feedthrough (430) is interposed between the electrical lines and the electronics. As described in U.S. Pat. No. 5,750,926, which is hereby incorporated by reference in its entirety, ceramic feedthroughs can provide a long term hermetic barrier that prevents ingress of gasses or liquids while maintaining electrical conductivity. According to one illustrative embodiment, the ceramic feedthrough (430) includes multiple ceramic layers. In the embodiment illustrated in FIG. 4, the ceramic feedthrough (430) includes four ceramic layers. A number of conductive vias (440) are placed within the ceramic layers. The conductive vias (440) are connected by conductive interlayers (450) to form a circuitous conduction path through the multilayer ceramic feedthrough (430). This circuitous conduction path increases the resistance to fluid ingress through the multilayer ceramic feedthrough (430), while maintaining electrical connectivity between the wired connections of the antenna (187) and the cochlear lead (190).

The circuitous conduction path terminates on either side of the multilayer ceramic feedthrough (430) in a bonding pad. The bonding pad allows the connection of an electrical component or wire. According to one illustrative embodiment, a number of electrical components (480) are attached to bonding pads on the upper surface of the multilayer ceramic feedthrough (430) and a number of wires (402) are connected to the lower surface. In this manner, the electrical components can receive signals, power, and output modified signals through the multilayer ceramic feedthrough (430) while being hermetically isolated from body fluids.

For example, external antenna (187) receives radio frequency signals from the headpiece (110, FIG. 2) and communicates these signals through wires to the electronic circuitry (480) within the internal processor (185). The signals are modified by the electrical components (480) and conducted out of the hermetically sealed chamber and into the cochlear lead (190, FIG. 3).

In one illustrative embodiment, the ceramic feedthrough (430) is formed from ceramic green-sheets. The ceramic green-sheets can be formed by tape casting or a variety of other methods. The ceramic green-sheets are further formed to have a number of apertures which are filled with conductive material. By way of example and not limitation, the conductive material may contain transition metals, rare-earth metals, alkali metals, alkaline-earth metals, and rare metals. The conductive material may be in the form of a paste, powder, or other suitable form.

One or more conductive interlayers (450) are disposed in between the ceramic layers to connect various filled apertures. The assembled ceramic green-sheets are then sintered or co-fired at an elevated temperature. During the firing process, the ceramic layers are fused into a monolithic ceramic feedthrough with a number of circuitous conductive pathways as shown in FIG. 4.

The ceramic feedthrough has a number of advantages that make it particularly suitable for hermetic seal. Ceramics can be constructed with very low moisture permeability, either by liquids or gasses. By way of example and not limitation, ceramic made primarily of silica can form a relatively impermeable material. Additionally, ceramic can be formed which is an electrical insulator, has very high tensile strength, and is corrosion resistant.

According to one illustrative embodiment, the ceramic feedthrough (430) is then brazed to the second portion (470) of the feedthrough case (400). A number of brazing techniques can be used to form a hermetically sealed braze joint (460) between the feedthrough case (400) and the ceramic feedthrough (430). For example, the ceramic feedthrough (430) could be metalized in the braze area to provide a surface to which the braze material adheres. The metallization of the ceramic surface may be accomplished in a number of ways. By way of example and not limitation, conductive portions of ceramics can be coated by electroplating using nickel, copper, or other suitable metals or metal combinations. The materials use in implanted devices must be carefully selected for long term reliability and chemical stability. Particularly, the materials must not have significant adverse effects on the patient's health. For example, metal combinations with a large percentage of copper are typically avoided because of copper has a tendency to corrode when implanted, thereby releasing copper oxides and other copper derivatives into the surrounding tissues.

Additionally, metallization of nonconductive portions of the ceramic surface may be accomplished using vapor deposition and/or sputter coating. In an alternative embodiment, a metal hydride or active braze could be used to join the ceramic feedthrough (430) and the feedthrough case (400). The metal hydride and active brazes possess the ability to wet ceramic surfaces that have not been previously metalized. For example a hydride, usually of titanium or zirconium, is reduced and brazed simultaneously in a controlled atmosphere. In one embodiment, following the metal hydride application, a silver, gold, copper, or copper/silver eutectic braze alloy can then used. By way of example and not limitation, a braze preform comprising approximately 82% gold and 18% nickel can be used to form the braze joint.

Active metal brazing is similar to the metal hydride process in that it contains an active element that reacts with the ceramic, thereby forming a reaction layer between the ceramic and the molten braze that will reduce the interfacial energy such that wetting of the ceramic takes place. However, active metal brazing is a single step process which can result in a reduction in assembly costs. By way of example and not limitation, these active elements may include titanium, zirconium, hafnium, vanadium, and aluminum or combinations thereof. According to one illustrative embodiment, the active braze material may be approximately 50% titanium and 50% nickel.

According to one embodiment, the braze joint may incorporate ceramic particulates. These ceramic particulates can increase the strength of the braze material, decrease its permeability, and reduce its coefficient of thermal expansion to more closely match the ceramic material. In one embodiment, the inclusion of as little of 5% (by volume) of ceramic particulates increases the strength of the reinforced active metal alloy over un-reinforced active metal alloy by approximately 30%. By including ceramic particulates in the braze joint, the joint is less likely to fail when subjected to temperature extremes or other forces.

For example, subsequent manufacturing processes, such as welding and soldering, may heat the ceramic and or titanium components of the case. The inclusion of ceramic particulates provides a braze material with an intermediate coefficient of thermal expansion that is greater than the ceramic but lower than the adjoining metal. The braze joint then acts as a buffer which reduces the thermal stress at any one surface and makes the joint less likely to fail at either the metal or ceramic interface.

The braze joint (460) connects the perimeter of the ceramic feedthrough (430) to the second portion (470) of the feedthrough case (400). The radial distance through the braze joint (460) is significant, creating a more formidable barrier to the ingress of exterior fluid or gasses. Additionally, the first portion (495) and second portion (470) may be relatively thin, thereby creating a flexure which allows for differential thermal expansion and isolates the ceramic feedthrough (430) and electronics (480) from impact.

A gap (497) may be left between the ceramic feedthrough (430) and the feedthrough case (400) to accommodate the flexure of the first portion (495) and second portion (470). By way of example and not limitation, the gap (497) may be useful to accommodate the differing thermal expansion of the ceramic feedthrough (430). Ceramic material typically has a relatively low coefficient of thermal expansion, while metals have relative higher coefficients of thermal expansion. Consequently, when the internal processor (185) or portions of the hermetically sealed enclosure experience a temperature change, the ceramic feedthrough (430) may expand and contract less than the feedthrough case (400).

For example, if the ceramic feedthrough (430) were forced into the feedthrough case (400) without a gap (497), a reduction in temperature of the internal processor (185) could cause the feedthrough case (400) to contract significantly more than the ceramic feedthrough (430), crushing the ceramic feedthrough (430) and/or damaging the braze joint (460). Additionally, the gap (497) may be useful in providing an area in which excess brazing material can flow without adverse results. According to one exemplary embodiment, the gap between the ceramic feedthrough (430) and the second portion of the feedthrough case (400) is between $\frac{1}{50}^{th}$ and $\frac{1}{100}^{th}$ of the major diameter or largest dimension of the ceramic feedthrough. For example, a case (400) which is approximately one inch in diameter could have a gap between 0.010 and 0.030 inches, and preferably 0.020 to 0.025 inches, in width. A variety of considerations could influence the sizing and placement of the gap, including but not limited to the amount of solder or braze flow expected into the gap, the amount of flexure desired in one or more directions, manufacturing considerations, and differences in material properties of the various materials.

Figure 5:
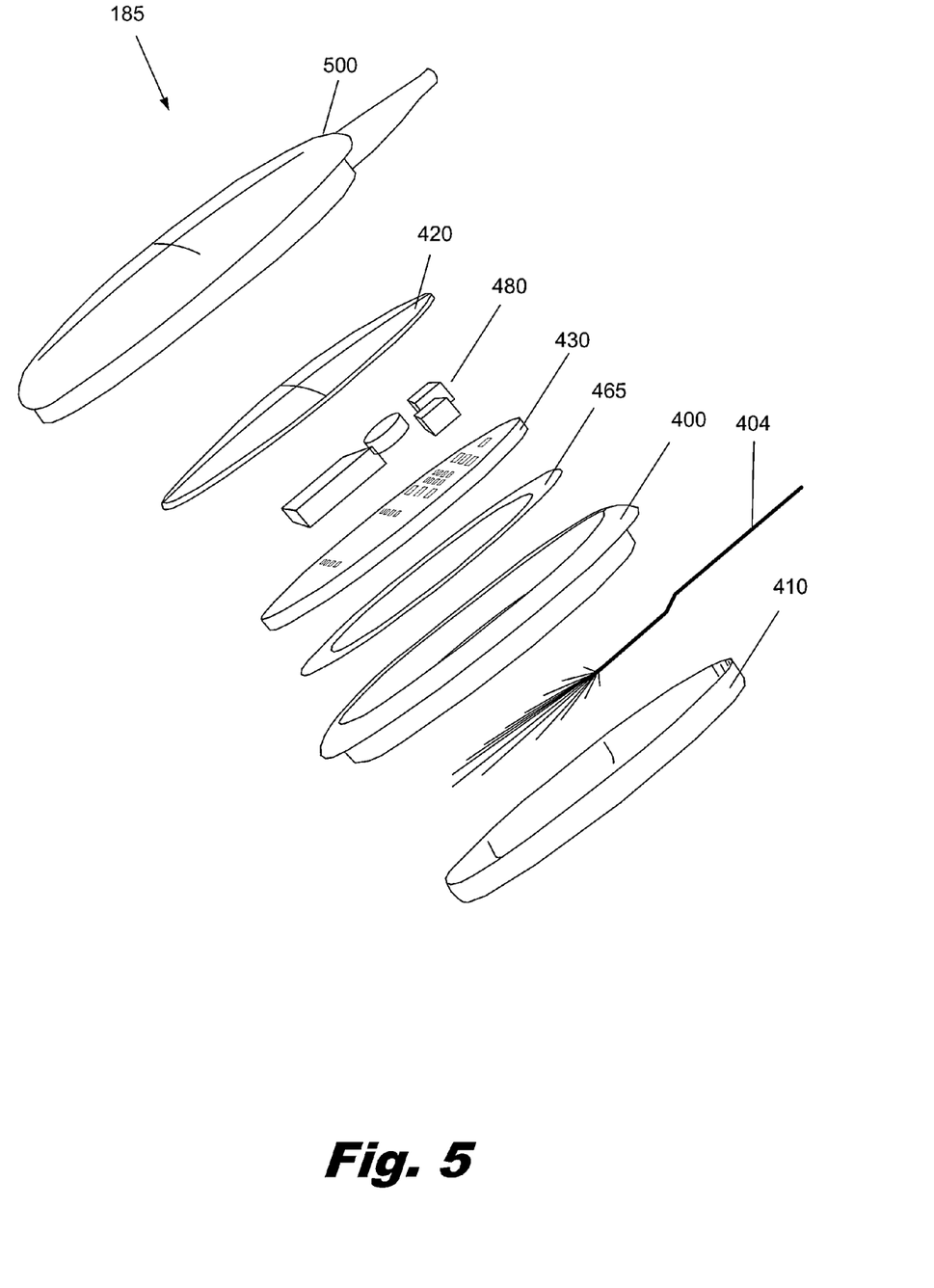
FIG. 5 is an exploded assembly view of an illustrative internal processor with a hermetically sealed feedthrough, according to one embodiment of principles described herein.

FIG. 5 is an exploded assembly view of the illustrative internal processor (185), including a top cover (420), a ceramic feedthrough (430), and a feedthrough case (400). The electronic components (480) are attached to the upper surface of the ceramic feedthrough (430). A preformed braze ring (465) is used to seal the ceramic feedthrough (430) to the feedthrough case (400), to form the braze joint (460, FIG. 4). A cable or coil (404) containing one or more wires attaches to the bond pads on the bottom of the ceramic feedthrough (430). A bottom cover (410) covers the lower portion of the case (400). As discussed above, a one piece biocompatible overcoat (500) may enclose the entire case. For example, the biocompatible overcoat (500) may be made from silicone and formed around the case (400) using liquid injection molding techniques. For simplicity, a number of features and components which may be present in a cochlear implant are not shown. For example, the antenna and its connections to the internal processor (185) are not shown in FIG. 5. As another example, a getter, which is not shown, may be located within the hermetically sealed case, such as adhered to the inside of the top cover (420).

Figure 6A:
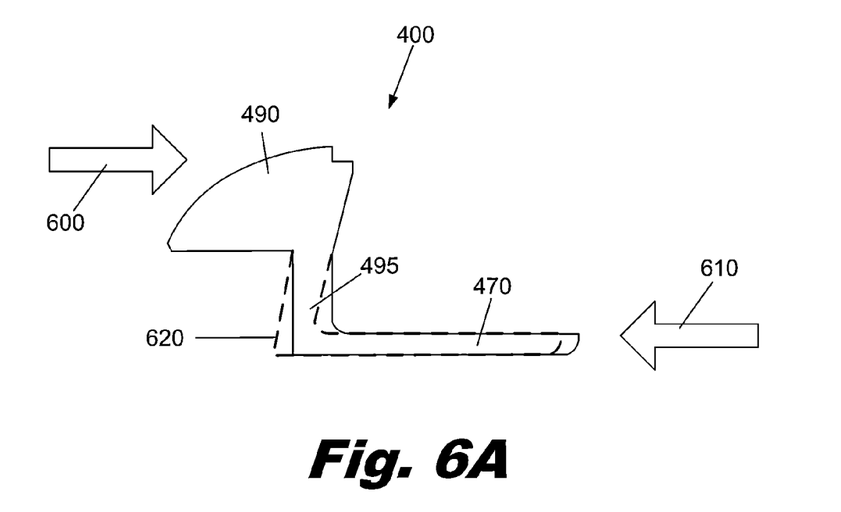
FIGS. 6A and 6B show an illustrative feedthrough case acting as a flexure to accommodate lateral forces applied to an internal processor, according to one embodiment of principles described herein.
Figure 6B:
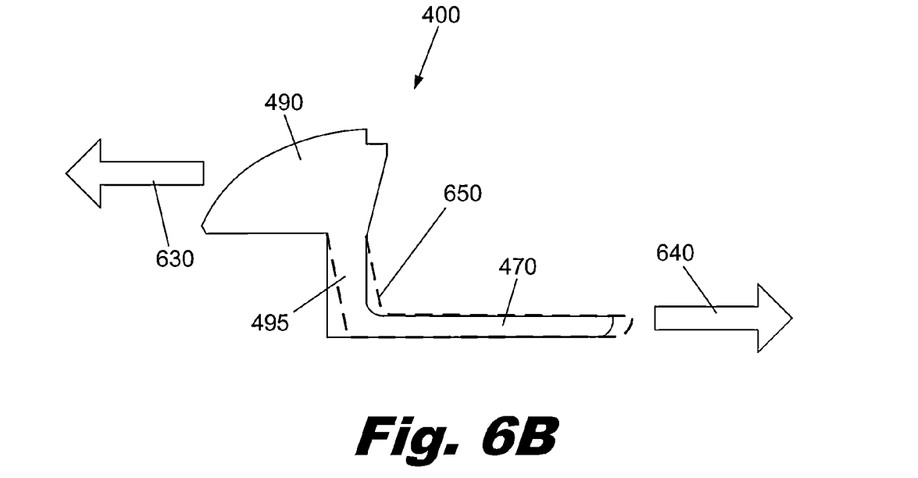

FIGS. 6A and 6B show an illustrative feedthrough case (400) acting as a flexure to accommodate lateral forces applied to an internal processor (185). In FIG. 6A, a lateral force to the left is illustrated by a first arrow (600) and an opposing lateral force to the right is illustrated by a second arrow (610). The lateral forces (600, 610) result in a lateral compression of the feedthrough case (400). According to one embodiment, the first portion (495) of the feedthrough case (400) is configured to flex in response to the applied lateral forces. One possible flexural mode is illustrated by the dashed profile (620).

In FIG. 6B, the lateral forces (630, 640) act in opposite directions, resulting in tension or elongation of the feedthrough case (400). Again, the feedthrough case (400) is configured to flex to accommodate the forces and allow displacement to minimize the effects of the forces (630, 640). One possible flexural mode is illustrated by the dashed profile (650).

The compressive and tensile forces illustrated in FIGS. 6A and 6B could arise as a result of a number of situations. One common situation may occur during one or more of the manufacturing operations required to assemble the internal processor (185). These compressive and tensile forces, if transmitted to the internal components such as the ceramic feedthrough (430) and braze joint (460), could result in damage and undesirable performance.

For example, during the brazing operation which joins the ceramic feedthrough (430) to the feedthrough case (400), the feedthrough case (400), the braze preform (465), and the ceramic feedthrough (430) may be heated to allow the braze preform (465) to form the braze joint (460). After forming the braze joint, the device is cooled. During cooling, the feedthrough case (400) may contract significantly more than a ceramic feedthrough (430). Consequently, if no accommodation for the differential thermal contraction were made, significant forces could be generated which could damage the braze joint or crush the ceramic feedthrough (430). The flexibility of the first and/or second portions of the feedthrough case (400) is designed to accommodate differential thermal contraction or expansion and minimize the forces transmitted to the ceramic feedthrough (430).

Figure 7A:
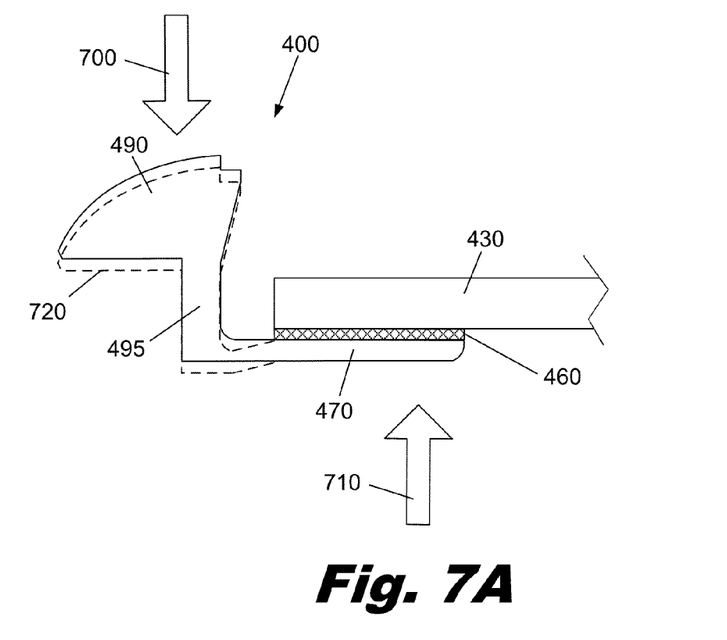
FIGS. 7A and 7B show an illustrative feedthrough case acting as a flexure to accommodate axial forces applied to an internal processor, according to one embodiment of principles described herein.
Figure 7B:
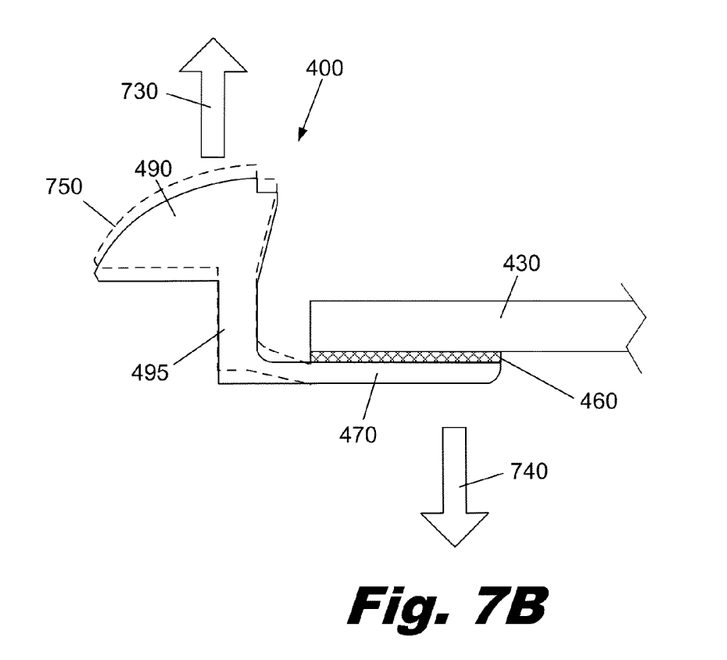

FIGS. 7A and 7B show an illustrative feedthrough case (400) acting as a flexure to accommodate vertical forces applied to a internal processor. In FIG. 7A, a downward vertical force is illustrated by a first arrow (700) and an opposing upward force is illustrated by a second arrow (710). The vertical forces (700, 710) result in a vertical compression of the feedthrough case (400). According to one embodiment, the second portion (470) of the feedthrough case (400) is configured to flex in response to the applied vertical forces. One possible flexural mode is illustrated by the dashed profile (720).

In FIG. 7B the vertical forces (730, 740) are acting in opposite directions, resulting in tension or elongation of the feedthrough case (400). Again, the feedthrough case (400) is configured to flex to accommodate the forces and allow displacement to minimize the effects of the forces (730, 740).

The vertical forces (700, 710, 730, 740) could arise as a result of a number of manufacturing steps or events. For example, when the internal processor (185) undergoes impact, the resulting impact and internal forces could result in vertical and/or lateral compressive forces. By using flexures incorporated into the feedthrough case (400) to isolate the braze joint (460), ceramic feedthrough (430), and electronics (480, FIG. 5), the robustness and reliability of the case (400) can be increased.

According to one embodiment, the flexure (495, 470) reduces the transmission of forces from the feedthrough case (400) to the ceramic feedthrough (430) in three independent axes. The flexural modes illustrated in FIGS. 6A and 6B may accommodate flexure in an X and Y direction, and flexural modes shown in FIGS. 7A and 7B may accommodate flexure in a Z direction. Consequently, the flexure (495, 470) is configured to allow for small amounts of relative motion between the ceramic feedthrough (430) and the feedthrough case (400) in three independent axes or combinations thereof, while still maintaining the integrity of the hermetic seal. Although FIGS. 6A, 6B, 7A, and 7B show specific modes which involve only one of the first portion (495) or second portion (470), a number of other flexure mode shapes could occur and be effective in minimizing transmitted forces.

According to one illustrative embodiment, the feedthrough case (400) is machined from titanium. The first portion (495) and second portion (470) could have relatively thin cross sections to allow for flexure. For example, the first and second portions (495, 470) may have a thickness of approximately 0.010 inches. If the feedthrough case (400) is made from other materials, such a stainless steel or other alloy, other cross sectional thicknesses could be calculated to provide the desired flexure and minimize the transmitted forces.

Other considerations could influence the geometry and thickness of the flexures, including but not limited to the mass that is attached to the flexure, the magnitude of the temperature changes the implantable device will be subject to, the magnitude of the impacts the implantable device is designed to accommodate, various manufacturing considerations, cost considerations, and the material properties of the materials that make up the implantable device.

Figure 8:
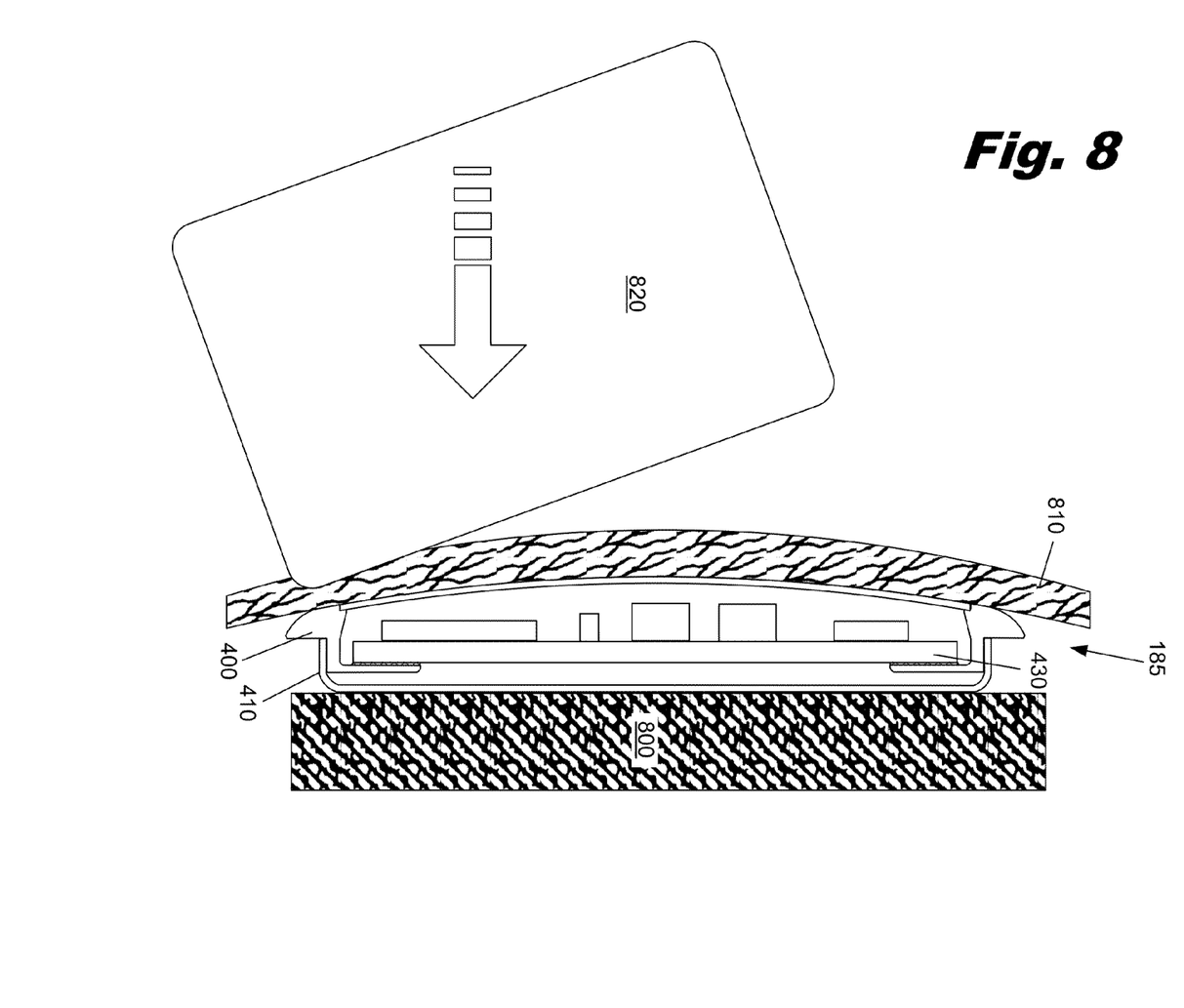
FIG. 8 is an illustrative diagram showing an illustrative hermetically sealed feedthrough case transferring impact loading to underlying tissue, according to one embodiment of principles described herein.

FIG. 8 is an illustrative diagram showing one illustrative internal processor (185) transferring impact loading to underlying tissue. As mentioned above, the internal processor (185) is typically surgically implanted beneath the skin (810) and resting on the skull (800) of the patient. The implantation site is typically above and behind the exterior ear. In the event of an impact of an exterior object (820) at the implantation site, it is desirable that the cochlear implant remains undamaged and transfers/distributes the impact forces to the underlying skull. Impact with exterior objects can occur for a variety of reasons. For example, impacts to the implantation site may occur in the course of normal activities such as riding a skateboard, playing football or baseball, or swimming.

According to one illustrative embodiment, forces generated by impacts to the top cover or feedthrough case are transmitted through the feedthrough case to the bottom cover and distributed to the underlying skull (800). As mentioned above, the first and second portions of the feedthrough case (400) act to isolate the sensitive interior components and braze joint from external forces, thereby reducing the likelihood of failure of the interior components or hermetic seals.

Figure 9:
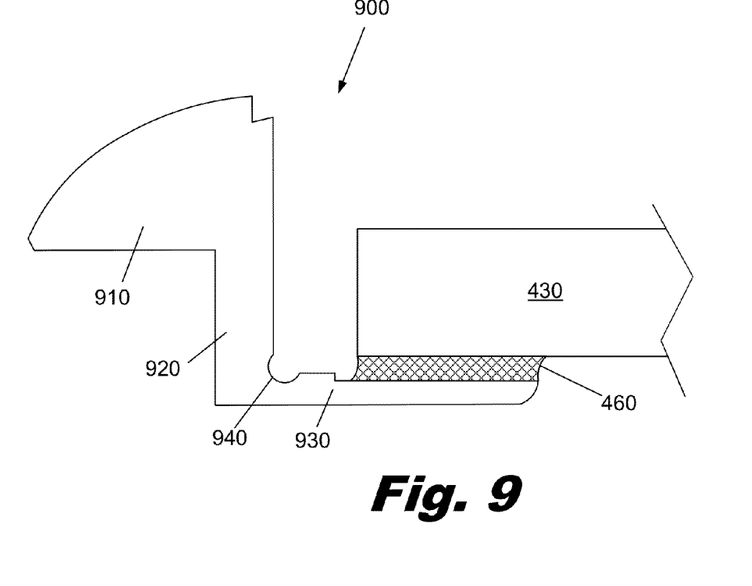
FIG. 9 is a diagram of an illustrative feedthrough case with a relief cutout to facilitate flexure, according to one embodiment of principles described herein.

The configurations of the feedthrough case illustrated above are only one example of possible geometries which could be used to form flexures and create a braze joint between a ceramic body and a flexure. FIG. 9 is a diagram of an illustrative feedthrough case (900) with a relief cutout (940) to facilitate flexure. In this embodiment, the body portion (910) of the feedthrough case (900) has a relatively large cross-section and serves as a primary structural component. The upper and lower covers could attach primarily to the body portion (910). The first portion (920) has a smaller cross section and extends downward from the body portion (910). A second portion (930) extends from the first portion (920) at a right angle toward the center of the implant. The braze joint (460) attaches the ceramic feedthrough (430) to the second portion (930).

To increase the flexibility of the first and second portions (920, 930), a relief cutout (940) can be formed at the junction of the first and second portions (920, 930). This relief cutout (940) could also serve to localize the flexure of the feedthrough case (900). Localization of the flexure could be advantageous in preventing separation of the bond joint from the second portion (930) of the feedthrough case and/or from the ceramic feedthrough (430).

Figure 10:
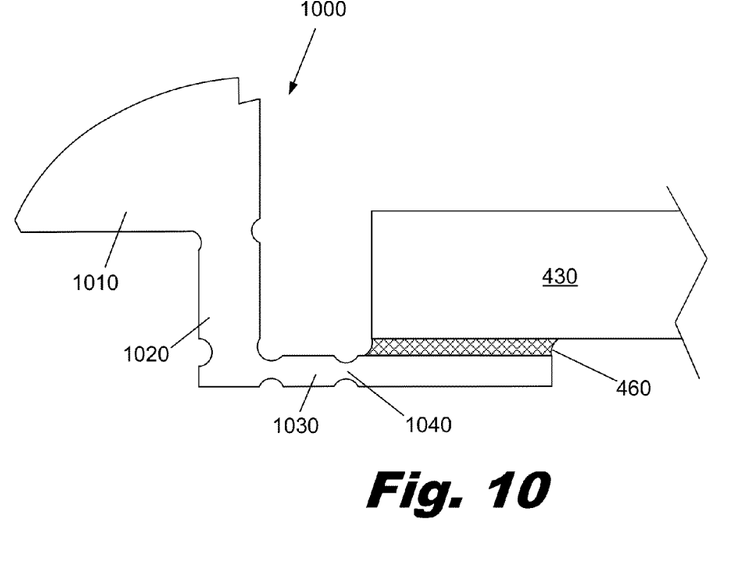
FIG. 10 is a diagram of an illustrative feedthrough case with a plurality of relief cutouts which create joints to facilitate flexure, according to one embodiment of principles described herein.

FIG. 10 is a diagram of an illustrative feedthrough case (1000) with a plurality of relief cutouts which create joints to facilitate flexure. As described above, a feedthrough case (1000) may have a body portion (1010), a first portion (1020) and a second portion (1030). A number of relief cutouts in the feedthrough case (1000) are used to create joints (1040) which have smaller cross-sections and lower stiffness than the adjoining areas. The joints (1040) allow the motion of the feedthrough case (1000) to be more precisely controlled when external forces are applied. The relief cutouts and joints can be configured to accommodate various materials, designs, and uses.

A number of illustrative embodiments of a feedthrough case and ceramic feedthrough have been described above. In designing hermetically sealed enclosure, there are a number of design parameters which can be altered to achieve the desired results for a given implantable device. For example, first portion (495) of the feedthrough case may be straight and vertical, straight and angled outward, straight and angled inward, curved inward or outward, or vertically straight in the bottom portion and angled inward in the top portion (as shown in most of the Figs.), etc. Additionally, in many situations it can be desirable to minimize one or more dimensions of the implanted device containing a hermetically sealed portion. For example, it can be desirable to minimized height of an internal processor used within a cochlear implant to avoid unnecessary protrusion from the skull. The feedthrough case, as illustrated in the examples above, can have a variety of features which minimize the overall height of the device. Another design parameter could be the effectiveness of the implant in transferring and distributing forces to underlying tissues, without damaging the implant or tissue. For example, in the illustrative embodiments shown above, external forces are transmitted from the upper cover to the feedthrough case and then to the bottom cover. This protects the internal components of the processor and distributes the force over a large area before transmitting the force to the underlying skull.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. An implantable medical device comprising:
  a hermetically sealed housing comprising:
    an interior cavity configured to receive electronics;
    a single piece metal housing component surrounding said electronics, said single piece metal housing component comprising:
      a structural body portion; and
      a flexure extending from said structural body portion, wherein said structural body portion and said flexure are integral elements of said single piece metal housing component;
    a ceramic feedthrough attached to said flexure; and
    a conductor passing through said ceramic feedthrough, wherein said sealed housing extends above and below said conductor, wherein extension of said sealed housing above and below said conductor protects said conductor from direct force applied to a top surface and a bottom surface of said sealed housing, and wherein said flexure reduces transmission of said force from said structural body portion to said ceramic feedthrough.

2. The implantable medical device of claim 1, wherein said housing component is made from one of: titanium and titanium alloy.

3. The implantable medical device of claim 1, wherein said flexure reduces said transmission of force in a radial direction and said transmission of force along an axis perpendicular to said radial direction.

4. The implantable medical device of claim 1, wherein said flexure comprises:
  a first portion, said first portion extending from said body portion in a first direction; and
  a second portion, said second portion extending from said first portion in a direction that is substantially perpendicular to said first direction.

5. The implantable medical device of claim 4, wherein said ceramic feedthrough comprises a planar bottom surface and a curved perimeter surface, wherein an outer perimeter of said planar bottom surface of said ceramic feedthrough is hermetically joined to said second portion such that a gap is interposed between said curved perimeter surface of said ceramic feedthrough and said first portion.

6. The implantable medical device of claim 5, wherein said gap is between $1/50^{th}$ and $1/100^{th}$ of a largest dimension of said ceramic feedthrough.

7. The implantable medical device of claim 4, further comprising a relief cutout in said flexure at an intersection of said first portion and said second portion.

8. The implantable medical device of claim 1, wherein said ceramic feedthrough comprises a multilayer ceramic structure having a plurality of vias and interlayers connecting said vias to create said conductor between a first planar surface of said ceramic feedthrough and an opposing second planar surface of said ceramic feedthrough.

9. The implantable medical device of claim 8, wherein said conductor further comprises bonding pads disposed on said first planar surface and said opposing second planar surface, electronic components bonded to said bonding pads disposed on said first surface, and wires bonded to bonding pads disposed on said second surface.

10. The implantable medical device of claim 1, further comprising an active braze joint, wherein said ceramic feedthrough is directly bonded to said flexure by said active braze joint such that said ceramic feedthrough is hermetically joined to said flexure.

11. The implantable medical device of claim 10, wherein said active braze joint comprises titanium.

12. The implantable medical device of claim 10, wherein a preformed braze ring is sandwiched between said ceramic feedthrough and said flexure, said preformed braze ring reacting with said ceramic feedthrough and bonding with said flexure to form said active braze joint between said feedthrough and said flexure.

13. A cochlear implant comprising:
  a single piece titanium feedthrough case comprising:
    a body portion;
    a first portion, said first portion extending from said body portion in a first direction; and
    a second portion, said second portion extending from said first portion in a direction that is substantially perpendicular to said first direction, said first portion and said second portion comprising a flexure, wherein said body portion, said first portion, and said second portion are integral elements of said single piece titanium feedthrough case; and
  a ceramic feedthrough wherein a first surface of said ceramic feedthrough is directly joined to said second portion by an active braze, said flexure reducing transmission of forces from said titanium feedthrough case to said ceramic feedthrough.

14. The cochlear implant of claim 13, wherein said ceramic feedthrough is hermetically joined to said second portion to form a gap between an inside perimeter surface of said body portion and an outer perimeter of said ceramic feedthrough; said gap between $1/50^{th}$ and $1/100^{th}$ of a largest dimension of said ceramic feedthrough.

15. The cochlear implant of claim 13, further comprising:
a titanium top cover; said titanium top cover being hermetically joined to said titanium feedthrough case using laser welding;
a titanium bottom cover; said titanium bottom cover being joined to said titanium feedthrough case using laser welding; and
a silicone overcoat, said silicone overcoat being applied using a liquid injection molding process such that said silicone overcoat substantially encapsulates said cochlear implant.

16. The implantable medical device of claim 10, wherein said active braze joint comprises titanium, nickel, and ceramic particulates, said titanium reacting with said ceramic feedthrough to form a reaction layer that reduces interfacial energy between said active braze joint and said ceramic feedthrough.

17. The cochlear implant of claim 13, wherein a relief cutout is formed at an intersection of said first portion and said second portion, said relief cutout increasing flexibility of said flexure and localizing bending in said flexure.

18. A hermetic housing for an implanted medical device, said hermetic housing comprising:
a housing component defining an outer perimeter of said hermetic housing, said metal feedthrough housing component comprising:
a first structural portion;
a second portion extending inwardly from said first structural portion, wherein said first structural portion and second portion are integral elements of said housing component; and
a relief cutout in said second portion to form a thin cross section flexure;
a ceramic body joined to said second portion;
a cover joined to the housing component to form a cavity; and
a conductor passing through said ceramic body, wherein a first end of the conductor is exposed inside the cavity and said housing component extends beyond a second end of said conductor so as to protect said conductor from application of direct force applied to a top surface and a bottom surface of said hermetic housing.

19. The housing of claim 18, wherein said ceramic body is directly joined to said second portion of said single piece metal housing component by a braze joint, and wherein said thin cross section flexure reduces transmission of said force from said structural portion to said ceramic body and conductor.

* * * * *